United States Patent [19]

Skidmore et al.

[11] Patent Number: 5,032,609
[45] Date of Patent: Jul. 16, 1991

[54] ETHANOLAMINE DERIVATIVES

[75] Inventors: Ian F. Skidmore, Welwyn; Harry Finch, Letchworth; Alan Naylor, Royston; Lawrence H. C. Lunts, Broxbourne; Charles Willbe; David Middlemiss, both of Bishop's Stortford, all of England

[73] Assignee: Glaxo Group Limited, London, England

[21] Appl. No.: 285,530

[22] Filed: Dec. 16, 1988

[30] Foreign Application Priority Data

Dec. 18, 1987 [GB] United Kingdom ............ 8729596

[51] Int. Cl.$^5$ .................. A01N 43/06; A61K 31/38; C07D 333/32; C07D 333/12
[52] U.S. Cl. ........................... 514/445; 514/446; 514/447; 514/448; 549/65; 549/66; 549/68; 549/70; 549/71; 549/72; 549/75; 549/76; 549/77
[58] Field of Search ............ 549/65, 66, 68, 70, 549/71, 72, 75, 76, 77; 514/445, 446, 447, 448

[56] References Cited

U.S. PATENT DOCUMENTS 4,730,008 3/1988 Skidmore et al. ............... 514/605

FOREIGN PATENT DOCUMENTS

| 82665A | 6/1983 | European Pat. Off. . |
| 0162576 | 11/1985 | European Pat. Off. . |
| 220054 | 4/1987 | European Pat. Off. . |
| 220878 | 5/1987 | European Pat. Off. . |
| 223410 | 5/1987 | European Pat. Off. . |
| 1203810A | 9/1970 | United Kingdom . |
| 2140800A | 12/1984 | United Kingdom . |
| 2159151 | 11/1985 | United Kingdom . |
| 2165542A | 4/1986 | United Kingdom . |
| 2182658A | 5/1987 | United Kingdom . |

Primary Examiner—Mary C. Lee
Assistant Examiner—Catherine S. Kilby Scalzo
Attorney, Agent, or Firm—Morgan & Finnegan

[57] ABSTRACT

The invention relates to compounds of general formula (I) and physiologically acceptable salts and solvates thereof, methods for their preparation and pharmaceutical formulations thereof.

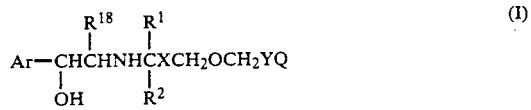

wherein

Ar represents a substituted phenyl or nitrogen-containing heterocyclic ring;

X and Y represent alkylene, alkenylene or alkynylene chains;

$R^1$, $R^2$ and $R^{18}$ each represent hydrogen or alkyl groups; and

Q represents an optionally substituted furan or thiophene ring.

The compounds of the invention have a stimulant action at $\beta_2$-adrenoreceptors and are useful in the treatment of diseases associated with reversible airways obstruction such as asthma and chronic bronchitis.

10 Claims, No Drawings

ETHANOLAMINE DERIVATIVES

This invention relates to novel ethanolamine derivatives having a stimulant action at $\beta_2$-adrenoreceptors, to processes for their preparation, to pharmaceutical compositions containing them and to their use in medicine.

Tehanolamine derivatives have previously been described as bronchodilators having stimulant activity at $\beta$-adrenoreceptors.

Thus, for example, UK Patent Specification No. 2140800A describes phenethanolamine compounds of the general structure

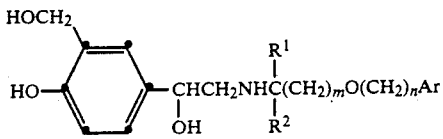

in which $R^1$ and $R^2$ each represent hydrogen or $C_{1-3}$alkyl; m is an integer 2 to 8; n is an integer 1 to 7; and Ar is an optionally substituted phenyl group.

UK Patent Specification No. 2162842A and European Patent Specification No. 0178919A describes aminophenol compounds of the general structure

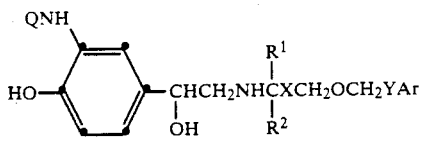

in which $R^1$ and $R^2$ each represented hydrogen of $C_{1-3}$alkyl; X represents a $C_{1-7}$ alkylene, $C_{2-7}$ alkenylene to $C_{2-7}$ alkynylene chain; Y represents a $C_{1-6}$ alkylene, $C_{2-6}$ alkenylene or $C_{2-6}$ alkynylene chain; Ar represents a phenyl group optionally substituted by one or more of a variety of specific substitutents; and Q represents a group $R^3CO-$, $R^3NHCO-$, $R^3R^4NSO_2-$, $R^5SO_2-$ where $R^3$ and $R^4$ each represent a hydrogen atom or a $C_{1-3}$alkyl group, and $R^5$ represents a $C_{1-4}$alkyl group.

UK Patent Specification 2165542A describes dichloroaniline derivatives of the general structure

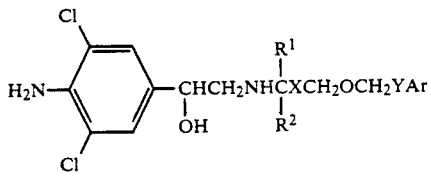

in which $R^1$ and $R^2$ each represent hydrogen or $C_{1-3}$alkyl, X represents a $C_{1-6}$alkylene, $C_{2-6}$alkenylene chain; Y represents a $C_{1-4}$alkylene, $C_{2-4}$alkenylene or $C_{2-4}$alkynylene chain; and Ar represent a phenyl group substituted by one or more of a variety of specific substituents.

We have now found a novel group of compounds which differ structurally from those of UK Patent Specification Nos. 2140800A, 2162842A and 2165542A, and European Patent Specification No. 0178919A, and which have a desirable and useful profile of activity.

Thus the present invention provides compounds of the general formula (I):

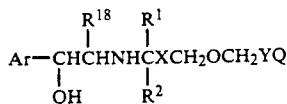

and physiologically acceptable salts and solvates (e.g. hydrates) thereof, wherein

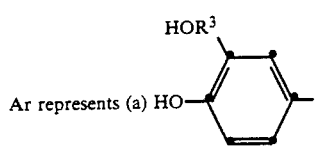

Ar represents (a)

(where $R^3$ is a straight or branched $C_{1-3}$alkylene group),

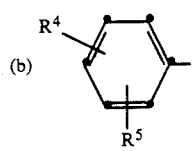

(b)

(where one of $R^4$ and $R^5$ is a hydroxy group and the other is a hydrogen or halogen atom or a hydroxy group),

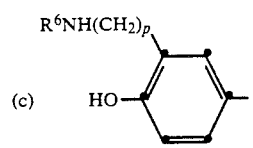

(c)

(where $R^6$ is a group $R^7CO-$, $R^7NHCO-$, $R^7R^8NSO_2-$, (where $R^7$ and $R^8$ each represent a hydrogen atom or a $C_{1-3}$alkyl group and $R^9$ is a $C_{1-3}$ alkyl group) and p is an integer 0 or 1),

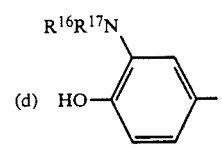

(d)

(where $R^{16}$ and $R^{17}$ each represent a hydrogen atom or a $C_{1-4}$ alkyl group, or, when $R^{16}$ is a hydrogen atom, $R^{17}$ may also represent a $C_{1-4}$ alkoxycarbonyl group),

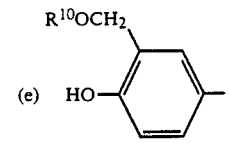

(e)

(where $R^{10}$ is a $C_{1-3}$ alkyl group),

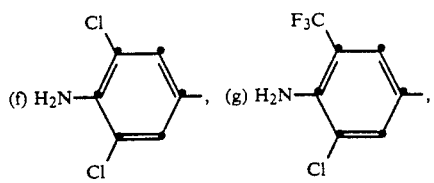

(f) , (g) ,

-continued

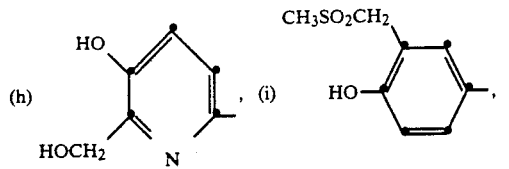

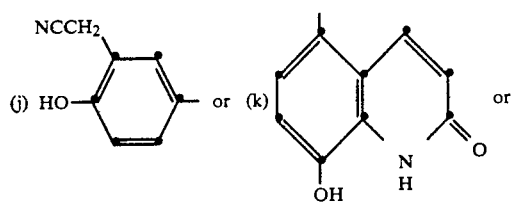

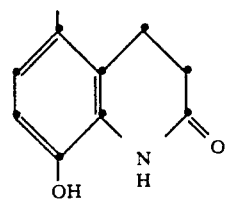

X represents a bond or a $C_1$, alkylene, $C_2$-, alkenylene or $C_2$-, alkynylene chain,
Y represents a bond or a $C_{1-6}$ alkylene, $C_{2-6}$ alkenylene or $C_{2-6}$ alkynylene chain, with the proviso that the sum total of carbon atoms in X and Y is 2 to 10;
$R^1$ and $R^2$ each represents a hydrogen atom or a $C_{1-3}$ alkyl group with the proviso that the sum total of carbon atoms in $R^1$ and $R^2$ is not more than 4;
$R^{18}$ represents hydrogen or $C_{1-3}$ alkyl;

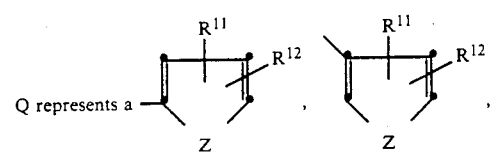

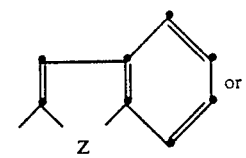

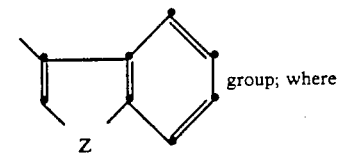 group; where

Z represents an oxygen or a sulphur atom;
$R^{11}$ represents a hydrogen or halogen atom or a group $C_{1-3}$ alkyl, nitro, $-(CH_2)_tR$, $-(CH_2)_rCOR^{13}$, or $SO_2NR^{14}R^{15}$;
$R^{12}$ represents a hydrogen atom or a $C_{1-3}$ alkyl group, or, when $R^{11}$ represents a halogen atom, $R^{12}$ additionally represents a halogen atom;
R represents a hydroxy, $C_{1-3}$ alkoxy or $NR^{14}R^{15}$ group;
$R^{13}$ represents a hydroxy, $C_{1-4}$ alkoxy or $NR^{14}R^{15}$ group;
$R^{14}$ and $R^{15}$ each represents a hydrogen atom or a $C_{1-4}$ alkyl group or $NR^{14}R^{15}$ forms a saturated heterocyclic amino group which has 5–7 ring members and optionally contains in the ring one or more atoms selected from $-O-$ or $-S-$ or a group $-NH-$ or $-N(CH_3)-$;
t represents an integer from 1 to 3;
r represents an integer from 0 to 3.

It will be appreciated that the compounds of general formula (I) possess one or more asymmetric carbon atoms. The compounds according to the invention thus include all enantiomers, diastereoisomers and mixtures thereof, including racemates. Compounds in which the carbon atom in the

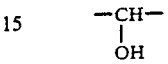

group is in the R configuration are preferred.

In the definition of general formula (I), the term alkenylene includes both cis and trans structures.

One preferred class of compounds of formula (I) are those wherein Z is 0. A further preferred class of compounds of formula (I) are those wherein Z is S. Conveniently Q is either

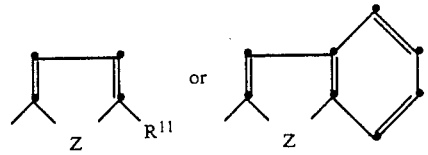

In the general formula (I), the chain X may be for example a bond, $-CH_2-$, $-(CH_2)_2$, $-(CH_2)_4-$, $-(CH_2)_5-$, $-CH_2C\equiv C$, $-(CH_2)_2CH=CH-$, $-(CH^2)^2C\equiv C-$, $-CH=CHCH^2-$, $-CH=CH(CHhd 2)_2-$ or $-CH_2C\equiv CCH_2-$. The chain Y may be for example a bond, $-CH_2-$, $-(CH_2)_2$, $-(CH_2)_3-$, $-CH_2)_4$, $-(CH_2)_5-$, $-(CH_2)_{(6}-$, $-CH=CH-$, $-C\equiv C-$, $-CH_2CH=CH-$ or $CH_2C\equiv C-$.

The total number of carbon atoms in the chains X and Y is preferably 4 to 10 inclusive and may be for example 4, 5, 6, 7, 8 or 9. Conveniently both X and Y are alkylene; X is conveniently a $C_3$ or $C_4$ alkylene; it is conveniently a $C_{1-5}$, for example $C_1$ or $C_2$ alkylene.

$R^1$, $R^2$ and $R^{18}$ may each be for example hydrogen atoms or methyl, ethyl, propyl or isopropyl groups. If one of $R^1$ and $R^2$ is a propyl or isopropyl group, the other is a hydrogen atom or a methyl group. $R^1$, $R^2$ and $R^{18}$ are each preferably a hydrogen atom or a methyl group. When $R^{18}$ represents a $C_{1-3}$ alkyl group, $R^1$ and $R^2$ preferably both represent hydrogen atoms.

A preferred group of compounds is that wherein $R^{18}$ represents a hydrogen atom.

Another preferred group of compounds is that wherein $R^1$ and $R^2$ are both hydrogen atoms, or $R^1$ is a hydrogen atom and $R^2$ is a $C_{1-3}$ alkyl group, particularly a methyl group, or $R^1$ is a methyl group and $R^2$ is a methyl group.

Conveniently $R^1$, $R^2$ and $R^{18}$ are all hydrogen.

In the definition of Ar in compounds of formula (I), $R^3$ may be, for example, $-CH_2-$, $-CH-$, $-(CH_2)_2-$ or $-(CH_2)_3-$.

"Halogen" in the definition of $R^5$ may be for example chlorine or fluorine. $R^7$ and $R^8$ may be, for example, a hydrogen atom or a methyl, ethyl, propyl or isopropyl group. $R^9$ may be a methyl, ethyl, propyl or isopropyl group. $R^{10}$ may be for example a methyl, ethyl or propyl group. $R^{16}$ and $R^{17}$ may each be for example a hydrogen atom or a methyl, ethyl, n-propyl, isopropyl, n-butyl, isobutyl, s-butyl or t-butyl group. Alternatively, when $R^{16}$ is a hydrogen atom, $R^{17}$ may be for example a methoxycarbonyl or ethoxycarbonyl group.

Ar in compounds of formula (I) may be for example

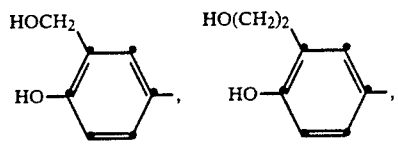

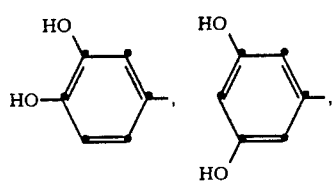

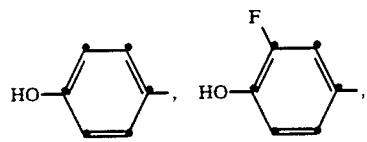

(where $R^6$ is HCO—, CH$_3$CO—,

NH$_2$CO—, (CH$_3$)$_2$NSO$_2$— or CH$_3$SO$_2$—),

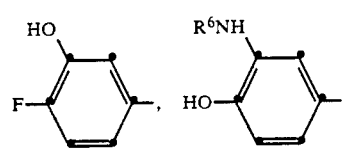

(where $R^6$ is as just defined),

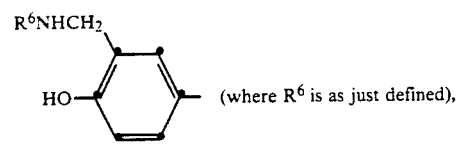

(where $R^{16}$ is hydrogen and $R^{17}$ is methyl),

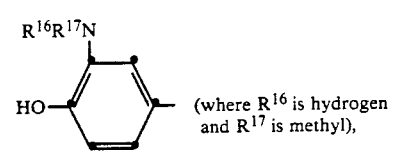

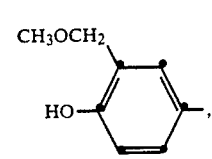

or a group of type (f), (g), (h), (i), (j) or (k).

The group Ar preferably represents

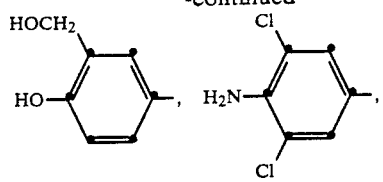

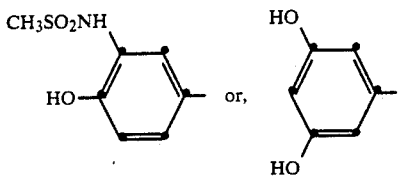

When —NR$^{14}$R$^{15}$ in compounds of formula (I) represents a saturated heterocyclic group, this may have 5, 6 or 7 ring members and optionally contain in the ring a heteroatom selected from —O— or —S—, or a group —NH— or —N(CH$_3$)—. Examples of such —NR$^{14}$R$^{15}$ groups are pyrrolidino, piperidino, hexamethylenimino, piperazino, N-methylpiperazino, morpholino, homomorpholino or thiemorpholino.

Examples of the substituents represented by the group $R^{11}$ are hydrogen, chlorine, fluorine or bromine atoms or methyl, ethyl, propyl, —CH$_2$OH, —CH$_2$N(CH$_3$)$_2$, —CH$_2$N(CH$_2$CH$_3$)$_2$, —COOH, —COOCH$_3$, —COO(CH$_2$)$_2$CH$_3$, —CONH$_2$, —CON(CH$_3$)$_2$, —CON(CH$_2$CH$_3$)$_2$, —CON or —SO$_2$N(CH$_2$CH$_3$)$_2$ groups.

The substituents $R^{12}$ may be for example a hydrogen atom, or a methyl, ethyl or propyl group or, when $R^{11}$ is a halogen atom, $R^{12}$ may be for example a chlorine, fluorine or bromine atom.

Particular examples of the group Q when Z is an oxygen atom are those in which $R^{11}$ represents hydrogen, $C_{1-3}$ alkyl (e.g. propyl), COR$^{13}$ (e.g. CO$_2$CH$_3$ or CO$_2$H), CH$_2$OH or —CONR$^{14}$R$^{15}$ (where R$^{14}$ and R$^{15}$ both represent $C_{1-4}$ alkyl e.g. ethyl groups) and $R^{12}$ represents hydrogen, or Q represents the group

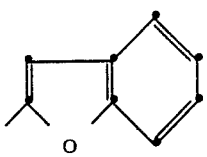

Alternatively, when Z is a sulphur atom, particular examples of the group Q are those in which $R^{11}$ represents hydrogen, chlorine alkyl(e.g. methyl), CONR$^{14}$R$^{15}$ (e.g. CONet$_2$), CH$_2$OH, COR$^{13}$ (e.g. CO$_2$CH$_3$, CO$_2$H) or SO$_2$NR$^{14}$R$^{15}$ (e.g. SO$_2$NEt$_2$) and $R^{12}$ represents hydrogen, or Q represents the group

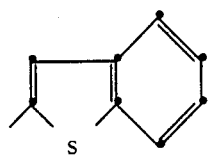

Preferred compounds according to the invention include α$^1$-[[[6-[[5-(2-furanyl)pentyl]oxy]hexyl]amino]-methyl]-4-hydroxy-1,3-benzenedimethanol; N-[5-[2-[[6-[[6-(2-furanyl)hexyl]oxy]hexyl]amino]-1-hydroxyethyl]-2-hydroxyphenyl]methanesulphonamide; 5-[3-[[6-[[2-(4-amino-3,5-dichlorophenyl)-2-hydroxyethyl]amino]hexyl]oxy]propyl]-N,N-diethyl-2-furancarboxamide;

4-hydroxy-$\alpha^1$-[[[6-[3-(3thienyl)proproxy]hexyl]amino]methyl]-1,3-benzenedimethanol; $\alpha^1$-[[[6-[2-(benzo[b]thienyl)ethoxy]hexyl]amino]methyl]-4-hydroxy-1,3-benzenedimethanol; 5-[1-hydroxy-2-[[6-[[4-(2-thienyl)butoxy]hexyl]amino]ethyl]-1,3-benzenediol; $\alpha^1$-[[[6-[2-[2-benzo[b]furanyl]ethoxy]hexyl]amino]methyl]-4-hydroxy-1,3-benzenedimethanol; N-[5-[2-[[6-[4-(2-benzo[b]furanyl)butoxy]hexyl]amino]-1-hydroxyethyl]-2-hydroxyphenyl]methanesulphonamide; 4-Hydroxy-$\alpha^1$-[[[6-[4-(2-thienyl)butoxy]hexyl]amino]methyl]-1,3-benzenedimethanol; $\alpha^1$-[[[1,1-dimethyl-6-[2-(2-thienyl)ethoxy]hexyl]amino]methyl]-4-hydroxy-1,3-benzenedimethanol; 5-[2-[[6-[[2-(4-amino-3,5-dichlorophenyl)-2-hydroxyethyl]amino]hexyl]-oxy]ethyl]-N,N-diethyl-2-thiophenecarboxamide; and their physiologically acceptable salts and solvates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, p-toluenesulphonates, naphthalenesulphonates, methanesulphonates, sulphamates, ascorbates, salicylates, acetates, diphenylacetates, triphenylacetates, fumarates, succinates, lactates, glutarates, gluconates, tricarballylates, hydroxynaphthalenecarboxylates e.g. 1-hydroxy- or 3-hydroxy-2-naphthalenecarboxylates, or oleates. The compounds may also form salts with suitable bases. Examples of such salts are alkali metal (e.g. sodium and potassium), alkaline earth metal (e.g. calcium or magnesium) salts, and salts with organic bases (e.g. triethylamine).

Salts having a very low solubility in water are particularly convenient where the compound is to be administered by inhalation or insufflation. Such salts includes diphenyl acetates, 4,4'-methylenebis 3-hydroxy-2-naphthalene carboxylates and 1-hydroxy- and 3-hydroxy-2-naphthalene carboxylates.

The compounds according to the invention have a selective stimulant action at $\beta_2$-adrenoreceptors, which furthermore is of a particularly advantageous profile. The stimulant action was demonstrated in the isolated trachea of the guinea-pig, where compounds were shown in cause relaxation of contractions induced by PGF $\alpha_2$ or electrical stimulation. Compounds according to the invention have shown a particularly long duration of action in these tests.

The compounds according to the invention may be used in the treatment of diseases associated with reversible airways obstruction such as asthma and chronic bronchitis.

The compounds according to the invention may also be used for the treatment of premature labour, depression and congestive heart failure, and are also indicates as useful for the treatment of inflammatory and allergic skin diseases, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichloro- tetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multidose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

In the following description relating to the preparation of compounds of formula (I) and intermediates used in the preparation thereof, X, Y, Ar, $R^1$, $R^2$, $R^{18}$ and Q are as defined for general formula (I) unless otherwise specified. Any hydroxy and/or amino groups present in the starting materials may need to be in a protected form and the final step may be the removal of a protecting group. Suitable protecting groups and methods for their removal are for example those described in "Protective Groups in Organic Chemistry", Ed. J. F. W. McOmie (Plenum Press, 1973), and "Protective Groups in Organic Synthesis", by Theodora Greene (John Wiley and Sons Inc, 1981). Thus hydroxyl groups may for example be protected by aralkyl groups such as benzyl, diphenylmethyl or triphenylmethyl, or as tetrahydropyranyl derivatives. Suitable amino protecting groups include aralkyl groups such as benzyl, α-methylbenzyl, diphenylmethyl or triphenylmethyl, and acyl groups such as acetyl, trichloroacetyl or trifluoroacetyl. Conventional methods of deprotection may be used. Thus for example aralkyl groups may be removed by hydrogenolysis in the presence of a metal catalyst (e.g. palladium on charcoal). Tetrahydropyranyl groups may be cleaved by hydrolysis under acidic conditions. Acyl groups may be removed by hydrolysis with a base such as sodium hydroxide or potassium carbonate, or a group such as trichloroacetyl may be removed by reduction with, for example, zinc and acetic acid.

In one general process (1), a compound of general formula (I) may be prepared by alkylation, using conventional alkylation procedures.

Thus, for example, in one process (a), a compound of general formula (I) in which $R^1$ is a hydrogen atom may be prepared by alkylation of an amine of general formula (II)

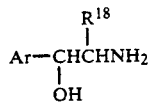
(II)

followed where necessary by removal of any protecting groups.

The alkylation (a) may be effected using an alkylating agent of general formula (III):

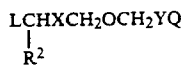
(III)

(wherein L represents a leaving group, for example a halogen atom such as chlorine, bromine or iodine, or a hydrocarbylsulphonyloxy group such as methanesulphonyloxy or p-toluenesulphonyloxy).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform at a temperature between ambient and the reflux temperature of the solvent.

According to another example (b) of an alkylation process, a compound of general formula (I) in which $R^1$ represents a hydrogen atom may be prepared by alkylation of an amine of general formula (II) with a compound of general formula (IV):

$$R^2COXCH_2OCH_2YQ \quad (IV)$$

in the presence of a reducing agent, followed where necessary by removal of any protecting groups.

Suitable reducing agents, when Z is an oxygen atom, include hydrogen in the presence of a catalyst such as platinum, platinum oxide, palladium, Raney nickel or rhodium, on a support such as charcoal, using an alcohol, e.g. ethanol or an ester e.g. ethyl acetate or an ether e.g. tetrahydrofuran, or water, as reaction solvent, or a mixture of solvents, e.g. a mixture of two or more of those just described at normal- or elevated temperature and pressure, for example for 20° to 100° C. and from 1 to 10 atmospheres. Alternatively, when Z is an oxygen or sulphur atom, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

Alkylation of an amine (II) with a compound of formula (IV) may result in formation of the intermediate imine of formula (V)

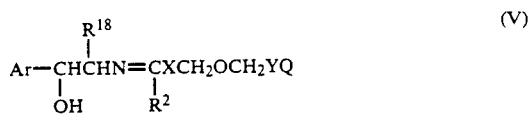
(V)

Reduction of the imine using the conditions described above, gives a compound of general formula (I).

In another general process (2), a compound of general formula (I) may be prepared by reduction. Thus, for example, a compound of general formula (I) may be prepared by reducing an intermediate of general formula (VI):

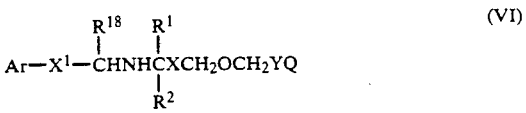
(VI)

(wherein $X^1$ represents a reducible group and/or Ar and/or Q contains a reducible group and the other(s) take the appropriate meaning as follows, which is $X^1$ is —CH(OH)— and Ar and Q are as defined in formula (I)), followed where necessary by removal of any protecting groups.

Suitable reducible groups include those wherein $X^1$ is a group >C=O, and Ar contains a substituent —CHO or —$CO_2R^{19}$ (where $R^{19}$ represents a hydrogen atom or an alkyl (e.g. $C_{1-3}$ alkyl) group).

The reduction may be effected using reducing agents conveniently employed for the reduction of carboxylic acids, aldehydes, esters and ketones.

Thus for example when $X^1$ in general formula (VI) represents a >C=O group and/or Ar contains a substituent —CHO or —$CO_2R$ this may be reduced to a —CH(OH)— or —$CH_2OH$ group respectively using for example, a complex metal hydride such as lithium aluminum hydride. The reaction may be effected in a solvent such as an ether e.g. diethyl ether or tetrahydrofuran, or a halogenated hydrocarbon e.g. dichloromethane, at a temperature of 0° C. to the reflux temperature of the solvent. Alternatively, when Z is an oxygen atom and $X^1$ represents the group >C=O, this may be reduced to a —CH(OH)— group using hydrogen in the presence of a catalyst as previously described for process (1) part (b).

Compounds of formula (I) may also be prepared by a process comprising interconversion of one compound of formula (I) into another.

Thus for example a compound of formula (I) in which $R^{11}$ represents the group —$(CH_2)_rCOR^{13}$ where $R^{13}$ is hydroxy may be prepared by hydrolysis of the corresponding compound in which $R^{13}$ represents $C_{1-4}$ alkoxy. The hydrolysis may for example be carried out under basic conditions using e.g. sodium hydroxide.

According to a further example of an interconversion process, a compound of formula (I) in which $R^{11}$ represents —$(CH_2)_rNR^{14}R^{15}$ may be prepared by reducing the corresponding compound of formula (I) in which $R^{11}$ represents —$(CH_2)_rCONR^{14}R^{15}$ wherein r represents zero, 1 or 2. The reduction may be carried using for example a hydride reducing agent e.g. lithium aluminium hydride, in the presence of a suitable solvent, for example, an ether such as diethyl ether or tetrahydrofuran.

In the general processes described above, a compound of formula (I) obtained may be in the form of a salt, conveniently in the form of a physiologically acceptable salt. Where desired, such salts may be converted to the corresponding free acids using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or iso-propanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diestereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

The intermediate compounds of general formula (VI) in which $X^1$ represent a group >C=O may be prepared from a haloketone of formula (VII):

(where Hal represents a halogen atom, and any hydroxyl and/or amino group(s) in the group Ar may optionally be protected) by reaction with an amine of general formula (VIII)

(wherein $R^{20}$ is a hydrogen atom or, when Z is an oxygen atom, a group convertible thereto by catalytic hydrogenation).

The reaction may be effected in a cold or hot solvent, for example dimethylformamide, an ester such as ethyl acetate, or an ether such as tetrahydrofuran in the presence of a base such as diisopropylethylamine.

The amines of formula (II) and haloketones of formula (VII) are either known compounds or may be prepared by methods analogous to those used for the preparation of the known compounds.

Intermediates of formulae (III), (IV) and (VIII) may be prepared by methods analogous to those used for the preparation of known compounds. Suitable methods include those described in UK Patent Specification No. 2140800A and in the exemplification included hereinafter.

The following examples illustrates the invention. Temperatures are in 0° C. 'Dried' refers to drying using magnesium sulphate or sodium sulphate except where otherwise stated. Thin layer chromatography (t.l.c.) was carried out over $SiO_2$. Flash column chromatography (FCC) was carried out on silica (Merck 9385) using, unless otherwise stated, one of the following solvent systems: A-toluene:ethanol: 0.88 ammonia; B-ethyl acetate:methanol:triethylamine; C-toluene:ethanol:triethylamine; D-ethyl acetate:methanol:0.88 ammonia. The following abbreviations are used: THF—tetrahydrofuran; DMF—dimethylformamide; BTPC—bis(triphenylphosphine)palladium (II) chloride; DEA—N,N-diisopropylethylamine; TAB—tetra-n-butylammonium bisulphate.

Intermediate 1 referred to below is
α¹-(aminomethyl)-4-hydroxy-1, 3-benzenedimethanol.

Intermediate 2

2-[2-[(6-Bromohexyl)oxy]ethyl]furan

2-Furanethanol (2 g) in DMF (5 ml) was added dropwise to a suspension of sodium hydride (0.43 g) in DMF (20 ml). The mixture was stirred for 30 min and added dropwise to 1,6-dibromohexane (21.8 g). The resulting suspension was heated at 60°–70° for 18 h, poured into water (200 ml) and extracted with diethyl ether (3×100 ml). The dried extract was evaporated and the residue was purified on a column of silica eluted with cyclohexane. The resulting oil was fractionally distilled (Kugelrohr) to give the title compound as a colourless oil (1.7 g) b.p. 75°–80°/0.3 Torr.

Intermediate 3

5-Propyl-2-furanethanol

A solution of n-butyllithium in hexane (1.55M, 100 ml) was added over 5 min to a stirred solution of furan (10 g) and tetramethylethylenediamine (17.4 g) in dry THF (100 ml) at 0° under nitrogen. The mixture was stirred for 2 h at 0°, treated with iodopropane (25 g) over 15 min at 0° (reaction exothermic), and stirred at 20° for 1 h and at 23° for 1 h. The mixture was cooled to 0°, n-butyllithium (1.55M, 100 ml) was added over 10 min and the mixture stirred at 0° for a further 1 h. The mixture was cooled to −10°, treated with a solution of ethylene oxide (7 g) in dry THF (20 ml) over 15 min and stirred at −10° to 0° for 2 h and at 23° for 18 h. Water (200 ml) was added, the organic solvents removed in vacuo and the residue extracted with ether (3×200 ml). The extracts were washed with 0.5M hydrochloric acid (200 ml), 8% sodium bicarbonate (50 ml) and brine (50 ml), dried and evaporated in vacuo to give a brown oil which was distilled (Kugelrohr) to give the title compound as a pale-yellow oil (18.2 g) b.p. 191°–200°/15 Torr.

Intermediate 4

2-[[2-(6-Bromohexyl)oxy]ethyl]-5-propylfuran

A mixture of Intermediate 3 (3 g), 1,6-dibromohexane (14.5 g), TAB (0.35 g) and 50% aqueous sodium hydroxide (15 ml) was vigorously stirred at 23° under nitrogen for 7 h. The mixture was diluted with water (50 ml), extracted with ether (2×50 ml) and the extracts were washed with water (50 ml) and brine (50 ml), dried and evaporated in vacuo to give a yellow oil. Distillation (Kugelrohr) afforded the title compound as a pale-yellow oil (5.36 g) b.p. 192°–198°/3 Torr.

Intermediate 5

2-[[5-(6-Bromohexyl)oxy]pentyl]furan

A mixture of 1,6-dibromohexane (9 g), 2-furanpentanol (1.9 g), TAB (0.25 g) and 50% aqueous sodium hydroxide (30 ml) was vigorously stirred at 23° for 17 h, diluted with water (150 ml) and extracted with ether (2×50 ml). The extracts were washed consecutively with water (50 ml) and brine (50 ml), dried and evaporated in vacuo to give a pale-yellow oil (10.0 g) which was purified by FCC eluting firstly with cyclohexane (to remove excess dibromohexane) and then with cyclohexane-ethyl acetate (4:1). The product (3.7 g) was distilled (Kugelrohr) to afford the title compound as a colourless oil (3.4 g) b.p. 160–170/0.1 Torr.

Intermediate 6

2-[2-[(5-Bromopentyl)oxy]ethyl]benzo(b)furan

A mixture of 2-benzo(b)furanethanol (2.00 g), 1,5-dibromopentane (6 ml), 50% sodium hydroxide (7 ml) and TAB (0.2 g) was vigorously stirred at 24° for 21 h, then partitioned between water (50 ml) and ether (60 ml). The organic phase was washed with brine (50 ml), dried and evaporated in vacuo. The oily residue was purified by FCC eluting with hexane-diethyl ether (97:3) to give the title compound as a colourless oil (2.70 g), t.l.c. (hexane-diethyl ether 4:1) Rf 0.54.

Intermediate 7

2-[2-[(6-Bromohexyl)oxy]ethyl]benzo[b]furan

The title compound, as a colourless oil (2.75 g), t.l.c. (diethyl ether)Rf 0.61, was prepared from 2-benzo[b]furanethanol (2.00 g) and 1,6-dibromohexane (7 ml) by the method described in Intermediate 6, except that hexane-diethyl ether (9:1 then 1:1) was used as the FCC eluent.

Intermediate 8

2-[3-[(6-Bromohexyl)oxy]propyl]furan

The title compound, as a colourless oil (2.8 g) , t.l.c. (cyclohexane-diethyl ether 3:1) Rf 0.6, was prepared from 2-furanpropanol (2.0 g) and 1,6-dibromohexane (12.2 g) by the method described in Intermediate 6, except that cyclohexane followed by cyclohexane-diethyl ether (9:1) was used as the FCC eluent.

Intermediate 9

Methyl 5-[4-[(6-bromohexyl)oxy]-1-butynyl]-2-furancarboxylate

Nitrogen gas was bubbled through a solution of methyl 5-bromo-2-furancarboxylate (2.34 g), 4-[(6-bromohexyl)oxy]-1-butyne (2.34 g) and dicyclohexylamine (2.26 g) in acetonitrile (30 ml) for 15 min. BTPC (84 mg) and copper (I) iodide (15 mg) were added and the mixture was refluxed under nitrogen for 3 h, diluted with ether (200 ml), filtered and the filtrate evaporated in vacuo. The resulting brown oil was purified by FCC eluting with cyclohexane-diethyl ether (10:1) to give the title compound as a brown oil (2.51 g), t.l.c. (hexane-ether 10:1) Rf 0.21.

Intermediate 10

Methyl 5-[3-[(5-bromopentyl)oxy]-1-propynyl]-2-furancarboxylate

Methyl 5-bromo-2-furancarboxylate (1.49 g) was treated with 3-[(5-bromopentyl)oxy]-1-propyne (1.49 g) according to the method of Intermediate 9 to give the title compound as a yellow oil (0.97 g), t.l.c. (cyclohexane-diethyl ether 10:1) Rf 0.18.

Intermediate 11

5-[3-[(6-Bromohexyl)oxy]-1-propynyl]-N,N-diethyl-2-furancarboxamide

5-Bromo-N,N-diethyl-2-furancarboxamide (2.0 g) was treated with 3-[(6-bromohexyl)oxy]-1-propyne (1.87 g) according to the method of Intermediate 9 except that the reaction mixture was stirred under nitrogen at 60° for 4h, and hexane-ether (5:1 then 2:1 then 1:1) was used as the eluant for FCC. This afforded the title compound as a dark yellow oil (2.98 g), t.l.c. (diethyl ether) Rf 0.35.

Intermediate 12

5-[3-[(6-Bromohexyl)oxy]propyl]-N,N-diethyl-2-furan-carboxamide

A solution of Intermediate 11 (2.98 g) in ethanol (50 ml) was added to pre-hydrogenated 10% palladium on charcoal (50% aqueous paste, 1.1 g) in ethanol (50 ml) and hydrogenated. The mixture was filtered through hyflo and evaporated in vacuo and the oil residue taken up in dichloromethane (30 ml), filtered again and evaporated in vacuo to afford the title compound as a brown oil (2.70 g), t.l.c. (diethyl ether) Rf 0.37.

Intermediate 13

Methyl 5-[4-[(6-bromohexyl)oxy]butyl]-2-furancarboxylate

A solution of intermediate 9 (2.35 g) in methanol (100 ml) and charcoal (0.5 g) were refluxed on a steam bath for 15 min, filtered and the filtrate evaporated in vacuo to give a brown oil (2.35 g). A solution of the oil in methanol (100 ml) was hydrogenated over pre-reduced 10% palladium oxide on charcoal (50% aqueous paste, 600 mg) in methanol (10 ml). The mixture was filtered through hyflo and evaporated in vacuo to give the title compound as a yellow oil (2.3 g), t.l.c. (hexane-ether 9:1) Rf 0.16.

Intermediate 14

Methyl 5-[3-[(5-bromopentyl)oxy]propyl]-2-furancarboxylate

Intermediate 10 (0.9 g) in methanol (50 ml) was treated with charcoal (ca 0.5 g) and subsequently hydrogenated according to the method of Intermediate 13. Purification of the initial product by FCC eluting with cyclohexane-ether (10:1) gave the title compound as a colourless oil (0.37 g), t.l.c. (cyclohexane-ether 10:1) Rf 0.12.

Intermediate 15

5-[4-[(6-Bromohexyl)oxy]butyl]-2-furanmethanol

A solution of Intermediate 13 (1.0 g) in diethyl ether (10 ml) was added dropwise to a stirred suspension of lithium aluminium hydride (0.15 g) in diethyl ether (5 ml) at room temperature under nitrogen. The mixture was stirred at room temperature for 0.5 h and then carefully quenched successively with water (0.2 ml), sodium hydroxide (0.2 ml) and water (0.6 ml). The mixture was diluted with diethyl ether (100 ml), filtered through hyflo and evaporated in vacuo to give an oil. Purification by FCC eluting with hexane-ether (4:1) gave the title compound as a colourless oil (0.82 g), t.l.c. (hexane-ether 1:1) Rf 0.17.

Intermediate 16 referred to below is 4-amino-α-(aminomethyl)-3,5-dichlorobenzenemethanol.

Intermediate 17

6-(2-Furyl)-5-hexenol 6-(2-Furyl)-5-hexenoic acid (3.6 g) in ether (25 ml) was reduced according to the method of Intermediate 15, except that the reaction time was 1.5 h, and there was no purification by FCC. The title compound was obtained as a pale yellow oil (2.89 g), t.l.c. (hexane-ether 1:1) Rf 0.17.

Intermediate 18

2-Furanhexanol

A solution of Intermediate 17 (2.84 g) in ethanol (18 ml) was hydrogenated according to the method of Intermediate 12. The mixture was filtered through hyflo and evaporated in vacuo to afford a pale yellow oil (2.78 g), which was purified by FCC with ether eluent to give the title compound as a colourless oil (2.25 g), t.l.c. (ether) Rf 0.39.

Intermediate 19

2-[6-(6-Bromohexyl)oxy]hexyl]furan

A mixture of Intermediate 18 (1.52 g), 1,6-dibromohexane (4 ml), 50% sodium hydroxide solution (4 ml) and TAB (100 mg) was vigorously stirred for 22 h, diluted with water (25 ml) and extracted with ether (80 ml). The organic phase was dried and evaporated in vacuo. The residue was purified by FCC eluting with hexane followed by hexane-ether (19:1, 9:1) to afford the title compound as a colourless liquid (2.00 g), t.l.c. (hexane-ether 5:1) Rf 0.39.

Intermediate 20

6-[(6-Bromohexyl)oxy]-1-hexyne

5-Hexyn-1-ol (5 g) was treated according to the method of Intermediate 19 except that the reactants were stirred under nitrogen. FCC elution with hexane followed by hexane:ether (95:5) gave the title compound as a colourless oil. (7.7 g), t.l.c. (hexane:ether 2:1) Rf 0.80.

Intermediate 21

Methyl 5-[6-[(6-bromohexyl)oxy]-1-hexynyl]-2-furancarboxylate

Methyl 5-bromofuran-carboxylate (5.4 g) was treated with Intermediate 20 (6.88 g) according to the method of Intermediate 9 except that the reaction mixture was refluxed under nitrogen for 2 h. Purification by FCC eluting with hexane:ether (9:1) gave the title compound as a colourless oil (6.7 g), t.l.c. (hexane:ether 9:1) Rf 0.15.

Intermediate 22

Methyl 5-[6-[(6-bromohexyl)oxy]hexyl]-2-furancarboxylate

A mixture of Intermediate 21 (6.0 g) and charcoal (ca. 1 g) in ethanol (100 ml) was refluxed on a steam bath for 15 mins, filtered and the filtrate evaporated in vacuo. A solution of the residual oil in ethanol (150 ml) was hydrogenated over pre-reduced 10% palladium oxide on charcoal (50% aqueous paste, 1 g) catalyst. The mixture was filtered through hyflo and the filtrate was evaporated in vacuo to give an orange oil. Purification by FCC eluting with hexane-ether (7:1→5:1) gave the title compound as a colourless oil (5.17 g), t.l.c. (hexane:ether 5:1) Rf 0.28.

Intermediate 23

N,N-Diethyl-5-[6-[(6-bromohexyl)oxy]-1-hexynyl]-2-furancarboxamide

N,N-diethyl-5-bromo-2-furancarboxamide (1.5 g) was treated with 6-[(6-bromohexyl)oxy]-1-hexyne (1.59 g) and N,N-dicyclohexylamine (2.10 g) according to the method of Intermediate 9 except that the reaction mixture was refluxed under nitrogen for 3 h and FCC eluting with hexane followed by hexane:ether (4:1→1:1) gave the title compound as an orange oil (1.90 g), t.l.c. (hexane:ether 1:1) Rf 0.15.

Intermediate 24

N,N-Diethyl-5-[6-[(6-bromohexyl)oxy]hexyl]-2-furancarboxamide

Intermediate 23 (1.9 g) was treated according to the method of Intermediate 22 excluding the purification step. The title compound was obtained as an orange oil (1.84 g) t.l.c. (System A 40:10:1) Rf 0.68.

Intermediate 25

2-[4-[(6-Bromohexyl)oxy]butyl]benzo[b]furan

A mixture of 2-benzo[b]furanbutanol (2 g), 1,6-dibromohexane (7.7 ml), TAB (500 mg) in 50% w/v sodium hydroxide solution (100 ml) was stirred at room temperature overnight. Water (100 ml) was added and the mixture extracted with ethyl acetate (2×100 ml). The combined organic extracts were dried and concentrated to give an oil. Purification by FCC eluting with hexane:ethyl acetate, 100:0→95:5) gave the title compound as a clear oil (2.1 g) t.l.c. (ether) Rf 0.83.

Intermediate 26

2-[[4-(6-Bromohexyl)oxy]butyl]thiophene

A mixture of 1,6-dibromohexane (9.5 g), 2-thiophenebutanol (2.0 g), TAB 0.25 g) and 50% aqueous NaOH (8 ml) as vigorously stirred at 23° for 18 h. The mixture was diluted with water (50 ml), extracted with diethyl ether (2×50 ml) and the extracts washed with water (50 ml), and brine (50 ml) dried and evaporated in vacuo to give a yellow oil (11 g). Purification by FCC on silica eluting with cyclohexane and then cyclohexane-ethyl acetate (4:1), afforded a product (5.2 g) which was distilled in vacuo to give the title compound as a colourless oil (3.6 g) b.p. 185°-195°/0.8 torr. T.l.c. (ethyl acetate-cyclohexane 1:4) Rf 0.73.

Intermediate 27

5-Methyl-2-thienylpropanol

N-Butyllithium in hexane (1.5M; 35.6 ml) was added dropwise at room temperature under nitrogen to a solution of 2-methylthiophene (5.0 g) in dry THF (50 ml). After stirring for 2.25 h, oxetane (4.42 g) in dry THF (15 ml) was added dropwise and stirring continued for 22.5 h. Saturated ammonium chloride solution (200 ml) was added and the mixture extracted with diethyl ether (3×200 ml), dried and evaporated in vacuo to give an oil. Purification by FCC on silica gel with cyclohexane-diethyl ether (1:1) as eluent gave the title compound as a pale orange oil (1.4 g). T.l.c. (cyclohexane-diethyl ether 1:1) Rf 0.31.

Intermediate 28

2-[[3-(6-Bromohexyl)oxy]propyl]-5-methylthiophene

A mixture of Intermediate 27 (1.0 g), 1,6-dibromohexane (3 ml), TAB (0.3 g) and aqueous sodium hydroxide solution (50%, w/v, 10 ml) was stirred at room temperature for 19 h. The resulting emulsion was treated with water (50 ml), extracted with ether (2×100 ml, 50 ml) and the combined extracts were dried and evaporated in vacuo to give a yellow liquid (~5 g). Purification by FCC on silica gel using cyclohexane-diethyl ether (1:1) as eluent gave the title compound as a pale yellow oil (2.0 g), T.l.c. (cyclohexane-diethyl ether 1:1) Rf 0.66.

Intermediate 29

2-[[2-(5-Bromopentyl)oxy]ethyl]thiophene

A mixture of 2-(2-thienyl)ethanol (4.5 g), 1,5-dibromopentane (23.0 g), aqueous sodium hyroxide (50% w/v; 25 ml), and TAB (0.25 g) was stirred at room temperature for 18 h, diluted with water (50 ml), and extracted with diethyl ether (2×100 ml). The dried extract was evaporated and the residue was purified by FCC eluting with cyclohexane followed by cyclohexane-diethyl ether (9:1) to give the title compound as a colourless oil (7.0 g). T.l.c. (cyclohexane-diethyl ether 3:1) Rf 0.5.

Intermediate 30

2,2-Dimethyl-7-[2-(2-thienyl)ethoxy]heptanoic acid n-Butyllithium in hexane (1.6M; 27.5 ml) was added dropwise to diisopropylamine (4.4 g) in THF (10 ml) at −78° under nitrogen. The mixture was warmed to 0°, stirred for 40 min, and isobutyric acid (1.94 g) was added dropwise. The resulting suspension was stirred at room temperature for 4 h and Intermediate 29 (4.0 g) was added dropwise. The mixture was stirred for 16 h at room temperature, treated with hydrochloric acid (2M; 50 ml), and extracted with diethyl ether (2×100 ml). The dried extract was evaporated and the residue was purified by FCC eluting with cyclohexane-diethyl ether (3:1) to give the title compound as a colourless oil (3.0 g). T.l.c. (cyclohexane-diethyl ether 3:1) Rf 0.2.

Intermediate 31

1,1-Dimethyl-6-[2-(2-thienyl)ethoxy]hexanamine

Ethyl chloroformate (1.2 g) in acetone (5 ml) was added to a solution of Intermediate 30 (2.48 g) and triethylamine (1.1 g) in acetone (30 ml) and water (3 ml) at 0°. The mixture was stirred for 30 min at 0° and sodium azide (0.72 g) in water (10 ml) was added dropwise. The resulting suspension was stirred at room temperature for 1 h, diluted with water (50 ml), and extracted with toluene (2×100 ml). The dried extract was evaporated during 2 h at ca 75°/30 mmHg and the resulting isocyanate in tert-butanol (50 ml) was refluxed for 18 h. Tert-butanol was removed under reduced pressure and the residue was treated with trifluoroacetic acid (20 ml). The solution was stirred at room temperature for 1 h and trifluoroacetic acid was removed under reduced pressure. The residue was basified with aqueous sodium hydroxide (2M) and extracted with diethyl ether (2×100 ml). The dried extract was evaporated to give the title compound as a pale yellow oil (2.1 g). T.l.c. (cyclohexane-diethyl ether 3:1) Rf 0.1.

Intermediate 32

7-[2-(2-Thienyl)ethoxy]-2-heptanone

A solution of Intermediate 29 (3.0 g) in diethyl ether (15 ml) was added dropwise to magnesium (0.25 g). The mixture was stirred for 1 h and added dropwise during 90 min to acetic anhydride (2.25 g) in diethyl ether (10 ml) at −78°. The resulting suspension was stirred for 1 h at −78°, warmed to −10°, treated with saturated aqueous ammonium chloride (30 ml), and extracted with diethyl ether (2×50 ml). The diethyl ether extract was washed with aqueous sodium hydroxide (2M; 50 ml), water (50 ml), and brine (50 ml), dried and evaporated. The residue was purified by FCC eluting with cyclohexane-diethyl ether (3:1) to give the title compound as a colourless oil (1.4 g). T.l.c. (cyclohexane-diethyl ether 3:1) Rf 0.25.

Intermediate 33

2-[2-[(6-Bromohexyl)oxy]ethyl]benzo[b]thiophene

2-Benzo[b]-thiopheneethanol (2.20 g), 1,6-dibromohexane (2.59 ml), TAB (0.25 g), aqueous 12.5M sodium hydroxide (9 ml), and ether (20 ml) were stirred overnight at room temperature. The mixture was diluted with water (50 ml), extracted with ether (3×50 ml), and the combined, dried extracts were evaporated. The residual oil was purified by FCC eluting with cyclohexane-diethyl ether (100:0→98.2) to give the title compound as a colourless oil (2.73 g). Analysis Found: C, 56.55; H, 6.3; Br, 23.8; S, 9.4. $C_{16}H_{21}BrOS$ requires C, 56.3; H, 6.2; Br, 23.4; S, 9.4%.

Intermediate 34

2-[3-[(6-Bromohexyl)oxy]propyl]thiophene

A mixture of 2-thiphenepropanol (5 g), 1,6-dibromohexane (25 g), 50% aqueous sodium hydroxide (25 ml) and TAB (500 mg) was stirred at room temperature overnight. Water (100 ml) was added over and the mixture was extracted with ether (2×100 ml). The organic layer was dried and concentrated to an oil which was purified by FCC eluting with hexane to give the title compound as a colourless oil (6.6 g). T.l.c. (hexane-diethyl ester 9:1) Rf 0.50.

Intermediate 35

5-[3-[(6-Bromohexyl)oxy]propyl]-2-thiophenecarboxylic acid

Butyl lithium (1.6M in hexane, 19.5 ml) was added to a stirred solution of Intermediate 34 (9.5 g) in dry THF (100 ml) at −78° under nitrogen. The yellow solution was stirred for 30 min then added slowly to a stirred slurry of dry ice (~100 g) in dry THF (100 ml) at −78° under nitrogen. After the addition the reaction mixture was slowly brought to room temperature, stirred for 1 h then treated with 2N hydrochloric acid (100 ml). The THF was evaporated and the aqueous residue was extracted with ether (2×100 ml). The organic extracts were dried and concentrated to an orange semi-solid which was triturated with boiling hexane to give the title compound as a pale brown solid (7.1 g) m.p. 93°–95°.

Intermediate 36

Propyl 5-[3-[(6-bromohexyl)oxy]propyl]-2-thiophenecarboxylate

A mixture of Intermediate 35 (7.0 g), N,N-dicyclohexylcarbodiimide (4.15 g), 4-dimethylamino)pyridine (300 mg) and propanol (2.4 g) in dichloromethane (50 ml) was stirred at room temperature for 4 h. Ether (150 ml) was added, the precipitate was filtered off, the solvent was evaporated and the residual oil was purified by FCC eluting with cyclohexane-diethyl ether (19:1) to give the title compound as a yellow oil (6.8 g). T.l.c. (hexane-diethyl ether 9:1) Rf 0.19.

Intermediate 37

3-[3-[(6-Bromohexyl)oxy]propyl]thiophene

3-Thiophenepropanol (5 g) was treated according to the method of Intermediate 34 to give the title compound as a colourless oil (5.8 g). T.l.c. (hexane-diethyl ether 9:1) Rf 0.42.

Intermediate 38

2-[3-[(6-Bromohexyl)oxy]propyl]-5-chlorothiophene

Butyl lithium (1.6M in hexane, 10.2 ml) was added to a stirred solution of Intermediate 34 (5.0 g) in dry THF (50 ml) at −78° under nitrogen. The yellow solution was stirred at −78° for 30 min, a solution of hexachloroethane (3 g) in dry THF (10 ml) was added and the reaction mixture was stirred for 15 min at −78°. Saturated aqueous ammonium chloride (25 ml) was added, the mixture was warmed to room temperature, the phases were separated and the organic layer was dried and concentrated to an orange oil, which was purified by FCC eluting with toluene-hexane (3:7) to give the title compound as a pale yellow oil (2.5 g). T.l.c. (hexane-diethyl ether 9:1) Rf 0.42.

Intermediate 39

2-[2-[(6-Bromohexyl)oxy]ethyl]thiophene

A mixture of 2-thienylethanol (10.0 g), 1,6-dibromohexane (57.10 g) and TAB (1.3 g) in 40% sodium hydroxide solution (40 ml) was stirred vigorously under nitrogen at room temperature for 5 h. The mixture was diluted with water (400 ml) and extracted with diethyl ether (2×300 ml), dried and evaporated in vacuo to give an oil. Purification by FCC eluting with hexane-ether (100:0→95:5) gave the title compound as a colourless oil (19.28 g), t.l.c. (hexane-ether 9:1) Rf 0.39.

Intermediate 40

5-[2-[(6-Bromohexyl)oxy]ethyl]-2-thiophenecarboxylic acid n-Butyllithium in hexane (1.55M, 22.2 ml) was added to a stirred solution of 2-[2-[(6-bromohexyl)oxy]ethyl]-thiophene (10.0 g) and treated according to the method of Intermediate 35, except that the reaction mixture was brought to room temperature very slowly over 3.5 h. The combined organic extracts were dried and evaporated in vacuo to give a pink solid, which on recrystallization from ether-hexane gave the title compound as a pale-pink solid (8.34 g) m.p. 60°–61°.

Intermediate 41

5-[2-[(6-Bromohexyl)oxy]ethyl]-2-N,N-diethylthiophenecarboxamide

Isobutyl chloroformate (1.22 g) in acetonitrile (5 ml) was added dropwise over 5 min to a stirred solution of Intermediate 40 (2.5 g), triethylamine (7.5 ml) and acetonitrile (15 ml) at 0° C. After 30 min diethylamine (2.32 ml) was added and the solution stirred for a further 2 h, diluted with ether (50 ml) and filtered. The filtrate was evaporated in vacuo to give a brown oily solid, which was triturated with ether-hexane (ca 1:1) to give a solid and a brown oil. The oil was purified by FCC eluting with hexane-ether (1:1)→ethyl acetate to give the title compound as a colourless oil (0.60 g), t.l.c. (ether) Rf 0.67.

Intermediate 42

Methyl 5-[2-[(6-bromohexyl)oxy]ethyl]-2-thiophenecarboxylate

A solution of Intermediate 40 (3.25 g) in methanol (20 ml) containing concentrated sulphuric acid (2 ml) was stirred at reflux for 4 h. The solution was allowed to cool and then basified to pH 8, initially using 2N sodium hydroxide solution and then 8% sodium bicarbonate solution. The methanol was evaporated in vacuo and the residue extracted with ether (3×150 ml). The combined organic phases were washed successively with brine (100 ml), water (100 ml), dried and evaporated in vacuo to give the title compound as a brown oil (3.16 g), t.l.c. (ether) Rf 0.86.

Intermediate 43

5-[2-[(6-Bromohexyl)oxy]ethyl]-2-thiophenemethanol

A solution of Intermediate 42 (1.5 g) in diethyl ether (15 ml) was added dropwise to a stirred suspension of lithium aluminium hydride (0.23 g) in diethyl ether (5 ml) at room temperature under nitrogen. The mixture was stirred at room temperature for 40 minutes and then carefully quenched successively with water (0.25 ml), 2N sodium hydroxide (0.25 ml) and water (0.75 ml). The mixture was diluted with diethyl ether (100 ml), filtered through hyflo (washing with additional ethanol) and evaporated in vauco to give an oil. Purification by FCC eluting with hexane-ether (3:1) gave the title compound as a colourless oil (1.02 g), t.l.c. (hexane-ether 2:1) Rf 0.16.

Intermediate 44

N,N-Diethyl-5-(2-hydroxyethyl)]-2-thiophenesulphonamide n-Butyllithium in hexane (1.55M, 5.9 ml) was added dropwise to N,N-diethyl-2-thiophenesulphonamide (2.0 g) in THF (15 ml) at −78° under nitrogen. The solution was stirred at −78° for 30 min and ethylene oxide (1.61 g) in THF (6 ml) was added. The mixture was allowed to warm up to room temperature, stirred for 30 min, treated with saturated aqueous ammonium chloride (100 ml) and extracted with diethyl ether (3×100 ml). The dried organic extracts were evaporated in vacuo to give a brown oil. Purification by FCC eluting with ether-hexane (1:1) and ether gave the title compound as a brown oil (1.83 g), t.l.c. (ether) Rf 0.42.

Intermediate 45

5-[2-[(5-Bromopentyl)oxy]ethyl]-2-N,N-diethylthiophenesulphonamide

A mixture of Intermediate 44 (1.6 g), 1,5-dibromopentane (2.5 ml), TAB (0.5 g) and 40% sodium hydroxide solution (4 ml) was stirred under nitrogen for 6 h. The mixture was diluted with water (100 ml) and extracted with diethyl ether (2×100 ml), dried and evaporated in vacuo to give a brown oil. Purification by FCC eluting with hexane-ether 10:0→3:1) gave the title compound as a colourless oil (1.80 g), t.l.c. (hexane-ether 3:1) Rf 0.17.

EXAMPLE 1

$\alpha^1$-[[[6-[[2-(2-Furanyl)ethyl]oxy]hexyl]amino]methyl]-4-hydroxy-1,3-benzenedimethanol A mixture of Intermediate 2 (1 g), Intermediate 1 (1.35 g), potassium iodide (1 g), triethylamine (5 ml) and DMF (40 ml) was heated at 60° for 3 h and poured into water (500 ml). The resulting emulsion was extracted with ethyl acetate (3×150 ml) and the combined extracts were dried and evaporated. The semi-solid residue was triturated with ethyl acetate (50 ml) and diethyl ether (30 ml) to give the title compound as a white solid (0.3 g) m.p. 91°-93°.

Found: C,66.5;H,8.1;N,3.6;
$C_{21}H_{31}NO_5$ requires: C,66.8;H,8.3;N,3.7%

EXAMPLE 2

4-Hydroxy-$\alpha^1$-[[[6-[[[2-(5-propyl-2-furanyl)]ethyl]oxy]hexyl]amino]methyl]-1,3benzenedimethanol, hemihydrate A mixture of Intermediate 1 (1.75 g), Intermediate 4 (1 g) and DMF (15 ml) was heated at 75° under nitrogen for 2 h. The mixture was diluted with water (150 ml), extracted with ethyl acetate (3×50 ml) and the extracts were washed with water (50 ml) and brine (50 ml) dried and evaporated in vacuo to give a pale-brown oil (1.1 g). Purification by FCC on triethylamine deactivated silica using System B (90:10:1) as the eluent afforded an oil (0.48 g) which on trituration with a cold mixture of cyclohexane and diethyl ether (1:1) gave the title compound as an off-white solid (0.41 g) m.p. 65°-66°.

Analysis Found: C,67.2;H,8.8;N,3.2.
$C_{24}H_3/NO_5.\frac{1}{2}H_2O$ requires C,67.2;H,8.9;N,3.3%.

EXAMPLE 3

$\alpha^1$-[[[6-[[5-(2-Furanyl)pentyl]oxy]hexyl]amino]methyl]-4-hydroxy-1,3-benzenedimethanol A mixture of Intermediate 5 (1 g), Intermediate 1 (0.87 g) and DEA (0.48 g) in DMF (10 ml) was heated at 75° for 1.5 h. Water (150 ml) was added and the mixture acidified to pH3 with 2M hydrochloric acid, then basified to pH8 with solid potassium bicarbonate and extracted with ethyl acetate (3×70 ml). The extracts were washed with water (50 ml), brine (50 ml), dried and evaporated in vacuo to give an oil (1.3 g) which was purified by FCC (triethylamine deactivated silica) eluting with System B (85:15:1) to afford a colourless oil (0.51 g). Trituration with cold ether for 24 h gave the title compound as a white powder (0.31 g) m.p. 50°-60°.

Analysis Found: C,68.3;H,8.9;N,3.2.
$C_{24}H_3/NO_5$ requires C,68.7;H,8.9;N,3.3%.

EXAMPLE 4

4-Amino-α-[[[5-[2-[2-benzo(b)furanyl]ethoxy]pentyl]amino]methyl]-3,5-dichlorobenzenemethanol A mixture of Intermediate 16 (1.6 g). Intermediate 6 (1.5 g) and DEA (1 ml) in DMF (16 ml) was heated at 100° for 3 h, cooled and evaporated in vacuo. The residual oil was purified by FCC eluting with System C (94:5:1) followed by System C (90:10:1) to give a gum. Trituration with hexane (20 ml) afforded the title compound as colourless crystals (1.22 g) m.p. 49°–52°.

Analysis Found: C,60.1;H,6.1;N,6.0; Cl,15.6.
$C_{23}H_{28}Cl_2N_2O_3.0.5H_2O$ requires C,60.0;H,6.35;N,6.1;Cl,15.4%.

Examples 5–9 were prepared according to the method of Example 4.

EXAMPLE 5

α$^1$-[[[6-[2-[2-Benzo(b)furanyl]ethoxy]hexyl]amino]methyl]-4-hydroxy-1,3 benzenedimethanol From Intermediate 1 (1.20 g) and Intermediate 7 (1.43 g), except that System A (39:10:1) was used as eluent for the FCC purification. The title compound was obtained as a pale yellow powder (606 mg) m.p. 101°–104°.

Analysis Found: C,70.1; H,7.75; N,3.2.
$C_{25}H_{33}NO_5$ requires: C,70.2; H,7.8; N,3.3%.

EXAMPLE 6

4-Amino-3,5-dichloro-α-[[[6-[3-(2-furanyl)propoxy]hexyl]amino]methyl]benzenemethanol From Intermediate 16 (0.8 g) and Intermediate 8 (0.7 g), except that hexane-ethanol-0.88 ammonia (44:5:1) was used as the FCC eluent, and the resulting gum was dissolved in ethyl acetate (30 ml) and washed with 8% sodium bicarbonate solution (15 ml), water (2×20 ml), brine (20 ml), dried and evaporated in vacuo, before triturating the residue with hexane. The title compound was obtained as colourless crystals (192 mg) t.l.c. (System A 39:10:1) Rf 0.5.

Analysis Found: C,58.1;H,6.9;N,6.5.
$C_{21}H_{30}Cl_2N_2O_3.0.2H_2O$ requires C,58.25;H,7.1;N,6.5%.

EXAMPLE 7

5-[3-[[6-[[2-(4-Amino-3,5-dichlorophenyl)-2-hydroxyethyl]amino]hexyl]oxy]propyl]-N,N-diethyl-2-furancarboxamide, (E)-butenedioate salt (2:1)

From Intermediate 16 (1.02 g) and Intermediate 12 (1.2 g). FCC purification with System C (95:3:2) and (93:5:2) eluants gave a product which was taken up in methanol (15 ml) and fumaric acid (133 mg) was added. The solution was evaporated in vacuo and the residue triturated with dry ether (x3) to afford the title compound as a cream powder (735 mg) m.p. 100°–103°.

Analysis Found: C,57.3; H,7.1; N,6.8; Cl,12.1.
$C_{26}H_{39}Cl_2N_3O_4.0.5C_4H_4O_4$ requires C,57.3; H,7.05; N,7.2; Cl,12.4%.

EXAMPLE 8

Methyl 5-[3-[[5-[[2-(4-amino-3,5-dichlorophenyl)-2-hydroxyethyl]amino]pentyl]oxy]propyl]-2-furancarboxylate From Intermediate 16 (1.84 g) and Intermediate 14 (1.85 g), with a reaction time of 1 h. FCC purification eluting with System C (95:5:1) gave a colourless oil, which was triturated with ether-hexane (1:10) to give the title compound as a white solid (1.31 g) m.p. 58°–59°.

Analysis Found: C,55.57;H,6.39;N,5.81;Cl,14.9.
$C_{22}H_{30}Cl_2N_2O_5$ requires C,55.82;H,6.39;N,5.92;Cl,15.0%

EXAMPLE 9

5-[4-[[6-[[2-[(4-Amino-3,5-dichlorophenyl)-2-hydroxyethyl]amino]hexyl]oxy]butyl]-2-furanmethanol From Intermediate 16 (0.75 g) and Intermediate 15 (0.75 g) with a reaction time of 2.5 h. FCC purification eluting with System C (95:5:1) afforded an oil which on trituration with hexane-ether (ca 4:1) gave the title compound as a white solid (367 mg) m.p. 60°–61°.

Analysis Found: C,58.6;H,7.3;N,6.0;Cl,15.0.
$C_{23}H_{34}Cl_2N_2O_4$ requires C,58.35;H,7.2;N,5.9;Cl,15.0%.

EXAMPLE 10

5-[3-[[5-[[2-(4-Amino-3,5-dichlorophenyl)-2-hydroxyethyl]amino]pentyl]oxy]propyl]-2-furanecarboxylic acid A solution of the product of Example 8 (0.60 g) in 2N sodium hydroxide solution (5 ml) and methanol (20 ml) was stirred under nitrogen for 3 h, then acidified to pH 6 with 2N hydrochloric acid. The solvent was evaporated in vacuo and the residue triturated with water (150 ml), and then ethyl acetate (2×100 ml). The residue was dissolved in methanol (200 ml) and evaporated in vacuo to give a white foam (0.55 g). Trituration with diethyl ether gave a white solid which was further triturated with hot isopropanol-methanol (ca 3:1). The mixture was filtered and evaporation of the filtrate in vacuo gave the title compound as a white solid (299 mg) m.p. 89°–91°, t.l.c. (System A 40:10:1) Rf 0.05.

Analysis Found: C,55.6;H,6.4;N,5.8;Cl,14.9.
$C_{22}H_{30}Cl_2N_2O_5$ requires C,55.8;H,6.4;N,5.9;Cl,15.0%

EXAMPLE 11

4-Amino-3,5-dichloro-α-[[[6-[3-[5-[(diethylamino)methyl]-2-furanyl]propoxy]hexyl]amino]methyl]benzenemethanol A solution of 5-[3-[[6-[[2-(4-amino-3,5-dichlorophenyl)-2-hydroxyethyl]amino]hexyl]oxy]propyl -N,N-diethyl-2-furancarboxamide (0.83 g) in benzene (6 ml) was added dropwise over 10 min to a stirred suspension of lithium aluminium hydride (175 mg) in dry ether (15 ml) under nitrogen. The mixture was stirred under nitrogen at 22° for 24 h, then quenched sequentially with water (1 ml), 2N sodium hydroxide solution (1 ml) and water (2 ml). The mixture was filtered through hyflo and the solids washed with toluene-ether (1:1, 10 ml). The combined filtrate and washings were dried and evaporated in vacuo to an oil. Purification by FCC eluting with System C (93:5:2) afforded the title compound as a pale yellow oil (0.59 g), t.l.c. (System A 39:10:1) Rf 0.5.

Analysis Found: C,60.9; H,8.2; N,8.2.
$C_{26}H_{41}Cl_2N_3O_3$ requires C,60.7; H,8.0; N,8.2%.

EXAMPLE 12

N-[5-[2-[[6-[[6-(2-Furanyl)hexyl]oxy]hexyl]amino]-1-hydroxyethyl]-2-hydroxyphenyl]methanesulphonamide, benzoate salt (1:1)

A solution of N-[5-(2-amino-1-hydroxyethyl)-2-hydroxyphenyl]methanesulphonamide (0.95 g), 2-[6-[(6- bromohexyl)oxy]hexyl]furan (0.84 g) and DEA (0.54 ml) in DMF (20 ml) was heated at 90° for 5 h, then evaporated in vacuo. The residue was purified by FCC with System A (39:10:1) eluant to afford a product which was dissolved in methanol (6 ml) and treated with benzoic acid (21 mg). The solvent was evaporated in vacuo and the residue triturated with dry ether to give the title compound as a beige solid (75 mg), t.l.c. (System A 39:10:1) Rf 0.15.

Analysis: Found: C,60.3; H,7.3; N,4.6.
$C_{32}H_{46}N_2O_8.H_2O$ requires C,60.4; H,7.6; N,4.4%.

EXAMPLE 13

Methyl 5-[6-[[6-[[2-hydroxy-2-[4-hydroxy-3-[(methanesulphonyl)amino]phenyl]ethyl amino]hexyl]oxy]hexyl]-2-furancarboxylate, benzoate salt A solution of [5-[2-amino-1-hydroxyethyl]-2-hydroxyphenyl]methanesulphonamide (0.95 g), methyl 5-[6-[(6-bromophenyl)oxy]hexyl]-2-furancarboxylate (1.00 g) and DEA (0.37 g) in DMF (20 ml) was stirred at ca 100° for 3 h. The solvent was evaporated in vacuo and the residue dissolved in methanol (15 ml) and absorbed onto silica (Merck 9385, 15 ml). Purification by FCC eluting with System A (40:10:1) gave a brown oil which was purified by FCC as above. The resulting brown oil in methanol (15 ml) was treated with benzoic acid (0.04 g), evaporated in vacuo and triturated with diethyl ether to give the title compound as a cream solid (0.203 g), m.p. 96°-98°.

Analysis: Found: C,57.7; H,6.9; N,4.2.
$C_{27}H_{42}N_2O_8S.C_7H_6O.1.5H_2O$ requires C,58.0; H,7.3; N,4.0%.

EXAMPLE 14

N,N-Diethyl-5-[6-[[6-[[2-hydroxy-3-[(methanesulphonyl)amino]phenyl]ethyl]amino]hexyl]oxy]hexyl]-2-furancarboxamide A solution of N-[5-[[2-amino-1-hydroxy]ethyl]-2-(hydroxy)phenyl]methanesulphonamide (0.98 g), N,N-diethyl 5-[6-[(6-bromohexyl)oxy]hexyl]-2-furancarboxamide (0.69 g) and DEA (0.25 g) was treated according to the method of Example 13 except the reaction time was 2 hours and treatment with benzoic acid was omitted. The title compound was obtained as a brown oil (0.141 g), t.l.c. (System A 40:10:1) Rf 0.1.

Analysis: Found: C,58.6; H,7.9; N,6.9.
$C_{30}H_{40}N_3O_7S.H_2O$ requires C,58.7; H,8.4; N,6.9%.

EXAMPLE 15

N-[5-[2-[[6-[[6-(2-Furanyl)hexyl]oxy]hexyl]amino]-1-hydroxyethyl]-2-hydroxyphenyl methanesulphonamide, 1-hydroxy-2-naphthoate salt A solution of N-[5-[2-[[6-[[6-(2-furanyl)hexyl]oxy]hexyl]amino]-1-hydroxyethyl]-2-hydroxyphenyl]methanesulphonamide, benzoate salt (426 mg) in methanol (4 ml) was partitioned between 8% sodium bicarbonate (15 ml) and ethyl acetate (40 ml) and the aqueous phase further extracted with ethyl acetate (20 ml). The combined organic extracts were dried and evaporated in vacuo to a gum which was taken up in methanol (5 ml). 1-Hydroxy-2-naphthoic acid (129.5 mg) was added, the solution evaporated in vacuo and the residue triturated with dry ether (×2) to give the title compound as an off-white solid (420 mg) m.p. 108°-109°.

Analysis: found: C,61.75; H,7.0; N,4.0.
$C_{25}H_{40}N_2O_6S.C_{11}H_8O_3.H_2O$ requires C,61.5; H,7.2; N,4.0%.

EXAMPLE 16

N-[5-[2-[[6-[4-(2-benzo[b]furanyl)butoxy]hexyl]amino]-1-hydroxyethyl]-2-hydroxyphenyl]methanesulphonamide benzoate (salt)

A solution of 2-[4-[(6-bromohexyl)oxy]butyl]benzo[b]furan (790 mg) [5-[2-amino-1-hydroxyethyl]-2-hydroxyphenyl]methanesulphonamide (1.07 g) and DEA (1.2 g) in DMF (20 ml) was stirred at 100° for 3 h. The solvent was evaporated in vacuo to leave a pale brown residue (2.2 g) which was purified by FCC eluting with System A (90:10:1→80:20:1) to give the base as a pale yellow oil (45 mg). A solution of this in methanol (10 ml) was treated with benzoic acid (11 mg), the solvent evaporated and the residue triturated under ether (10 ml) to give the title compound as a light brown solid (55 mg), m.p. 79°-80°.

Analysis: Found: C,62.3; H,7.1; N,4.5; S,5.0.
$C_{27}H_{38}N_2O_6S.C_7H_6O_2.0.85\ H_2O$ requires C,62.2; H,7.0; N,4.3; S,4.9%

EXAMPLE 17

N-[5-[2[[6-[4-(2-benzo[b]furanyl)butoxy]hexyl]amino]-1-hydroxyethyl]-2-hydroxyphenyl]methanesulphonamide 4,4'-methylenebis[3-hydroxy-2-naphthalene carboxylate]salt (2:1)

A solution of 2-[4-[(6-bromohexyl)oxy]butyl]benzo[b]furan (2.0 g) N-[5-(2-amino-1-hydroxyethyl)-2-hydroxyphenyl]methanesulphonamide (3.48 g) and DEA (1.0 ml) in DMF (25 ml) was heated at 80° under nitrogen, for 4 h, and the solvent was evaporated in vacuo to leave a dark brown oil. Purification by FCC eluting with System A (90:10:1) gave the free base as an immobile yellow oil (1.2 g). A portion of the base (341 mg) in methanol (20 ml) was heated under reflux with pamoic acid (170 mg) in methanol (5 ml) for 0.5 h. The clear solution was evaporated to give the title compound as a yellow foam (521 mg), m.p. 99°-101°.

Analysis: Found: C,63.9; H,6.5; N,3.7; S,4.25.
$C_{27}H_{38}N_2O_6S.\frac{1}{2}C_{23}H_{16}O_6.0.5H_2O$ requires C,64.1; H,6.6; N,3.9; S,4.4%.

EXAMPLE 18

4-Hydroxy-$\alpha^1$-[[[6-[4-(2-thienyl)butoxy]hexyl]amino]methyl]-1,3-benzenedimethanol A mixture of Intermediate 26 (1 g), DEA (0.45 g), Intermediate 1 (0.85 g) and DMF (10 ml) was heated at 75° for 2 h. The mixture was diluted with water, acidified to pH 3 with 2M HCl, basified to pH8 with solid sodium bicarbonate and extracted with ethyl acetate (2×80 ml). The extracts were washed with water (50 ml) and brine (50 ml) dried and evaporated in vacuo to give an oil (1.3 g) which was purified by FCC on triethylamine deactivated silica using System B (85:15:1) as the eluant to give the product as an oil (0.46 g). Trituration with cold diethyl ether gave the title compound as a white solid (0.33 g) m.p. 64°-65°.

Analysis Found: C,65.8;H,8.3;N,3.3
$C_{23}H_{35}NO_4S$ requires: C,65.5;H,8.4;N,3.4%.

EXAMPLE 19

4-Hydroxy-$\alpha^1$-[[[6-[3-(5-methyl-2-thienyl)propoxy]hexyl]amino]methyl]-1,3-benzenedimethanol A solution of Intermediate 28 (1.00 g), DEA (0.81 ml), Intermediate 1 (0.86 g) and DMF (10 ml) was heated at 75°-80° for 2.5 h. The mixture was diluted with water (100 ml), acidified to pH 3 with 2M hydrochloric acid, basified to pH8 with solid potassium hydrogen carbonate and extracted with ethyl acetate (3×50 ml). The combined extracts were washed with water (50 ml) and brine (50 ml), dried and evaporated in vacuo to give an oil which was purified by FCC on triethylamine deactivated silica using System B (80:10:1) as the eluent to give the product as a viscous oil. Trituration with cold ether gave the title compound as a white solid (460 mg) m.p. 59°-62°. T.l.c. (Et$_3$N deactivated SiO$_2$, ethyl acetate-methanol 8:1) Rf 0.24.

EXAMPLE 20

$\alpha^1$-[[[1,1-Dimethyl-6-[2-(2-thienyl)ethoxy]hexyl]amino]methyl]-4-hydroxy-1,3-benzenedimethanol,benzoate (salt)

A solution of methyl-5-(bromoacetyl)-2-hydroxybenzoate (1.93 g), Intermediate 31 (1.8 g), and DEA (0.9 g) in ethyl acetate (30 ml) was refluxed for 4H and evaporated. The residue was extracted with diethyl ether (50 ml) and the solution added dropwise to a suspension of lithium aluminium hydride (1.0 g) in diethyl ether (50 ml) at 0°. The mixture was stirred at room temperature for 3 h, treated cautiously with water (10 ml), acidified to pH1 with hydrochloride acid (2M), and basified to pH 8 with solid potassium carbonate. The resulting slurry was extracted with ethyl acetate (3×200 ml) and the dried extract was evaporated. The residue was purified by FCC eluting with System B (90:10:1) to give a yellow oil (0.3 g). The oil in chloroform (5 ml) was added to benzoic acid (0.2 g) in chloroform (5 ml) and the chloroform was removed by evaporation. The residue was triturated with diethyl ether (10 ml) to give the title compound as a cream solid (0.05 g) m.p. 85°-90°. T.l.c. (System D 9:1:0.1) Rf 0.2.

EXAMPLE 21

4-Hydroxy-$\alpha^1$-[[[1-methyl-6-[2-(2-thienyl)ethoxy]hexyl]amino]methyl]-1,3-benzenedimethanol.

A solution of Intermediate 1 (0.84 g), Intermediate 32 (1.1 g) and acetic acid (0.276 g) in methanol (20 ml) was treated with sodium cyanoborohydride (0.2 g) and stirred for 18 h under nitrogen. Saturated aqueous sodium bicarbonate (50 ml), was added and the mixture was extracted with ethyl acetate (3×50 ml). The dried extract was evaporated and the residue was purified by FCC eluting with System B (9:1:0.1) to give the title compound as a white solid (0.8 g) m.p. 68°-70°.

Analysis Found: C,64.8;H,8.2;N,3.3.
C$_{22}$H$_{33}$NO$_4$S requires C,64.8;H,8.2;N,3.4%.

EXAMPLE 22

$\alpha^1$-[[[6-[2-(Benzo[b]thienyl)ethoxy]hexyl]amino]methyl]-4-hydroxy-1,3-benzenedimethanol Intermediate 33 (1.55 g), Intermediate 1 (1.00 g), DEA (1.29 ml) and DMF (14 ml) were stirred at 95°-100° under nitrogen for 1 h. The cooled mixture was evaporated (1 Torr), treated with aqueous saturated sodium bicarbonate (50 ml), and extracted with ethyl acetate (3×50 ml). The combined, dried organic extracts were evaporated onto silica gel (Merck 7734, 5 g), and the resultant silica gel plug applied to an FCC column. Elution with System B (94:5:1→89:10:1) afforded, after trituration with ether, the title compound as a white solid (414 mg), m.p. 111°-114.5°. T.l.c. (NEt$_3$deactivated SiO$_2$, System B 89:10:1) Rf 0.06.

EXAMPLE 23

Propyl 5-[3-[[6-[[2-hydroxy-2-[4-hydroxy-3-(hydroxymethyl)-phenyl]ethyl]amino]hexyl]oxy]propyl]-2-thiophenecarboxylate hydrobromide A solution of Intermediate 36 (1.96 g) in dry DMF (3 ml) was added to a solution of Intermediate 1 (1.83 g) and DEA (2.6 g) in dry DMF (30 ml) at 100°. The solution was stirred for 3 h, the solvent was evaporated and the residue was purified by FCC eluting with System A (80:20:1) to give a brown oil (1.75 g). Trituration of this oil with diethyl ether gave the title compound as a cream solid (540 mg) m.p. 69°-71°.

Analysis Found: C,54.60; H,7.30; N,2.43; S,5.78.
C$_{26}$H$_{39}$NO$_6$S.HBr requires C,54.35; H,7.02; N,2.44; S,5.58%.

EXAMPLE 24

4-Hydroxy-$\alpha^1$-[[[6-[3-(3-thienyl)propoxy]hexyl]amino]methyl]-1,3-benzenedimethanol Intermediate 37 (1.53 g) was added to a stirred solution of Intermediate 1 (1.83 g) and DEA (2.6 g) in DMF (30 ml ) at 80° and the solution was stirred for 2 h. The DMF was evaporated and the residual oil was purified by FCC eluting with System A (80:21:1) to give an amber oil (1.4 g) which was triturated with ether to give the title compound as a white powder (900 mg) m.p. 86°-88°. T.l.c. (System A 80:20:1) Rf 0.24.

EXAMPLE 25

5-[1-Hydroxy-2-[[6-[4-(2-thienyl)butoxy]hexyl]amino]ethyl]-1,3-benzenediol, (E)-2-butenedioate (2:1) (salt)

A solution of intermediate 26 (800 mg) in dry DMF (1 ml) was added to a stirred solution of 5-(2-amino-1-hydroxyethyl)-1,3-benzendiol (700 mg) and DEA (1.29 g) in dry DMF (15 ml) at 100° and stirred at 100° for 2 h. The solvent was evaporated and the residue was purified by FCC eluting with System A (80:20:1) to give a straw coloured oil (550 mg). The oil in methanol (5 ml) was added to a solution of fumaric acid (100 mg) in methanol (5 ml), the methanol was evaporated and the residual oil was triturated with dry ether to give the title compound as an off-white powder (550 mg) m.p. 123°-124°. T.l.c. (System A 80:20:1) Rf 0.25.

EXAMPLE 26

N-[5-[2-[[6-[3-(5-Chloro-2-thienyl)propoxy]hexyl]amino]-1-hydroxyethyl]-2-hydroxyphenyl]methanesulphonamide A solution of Intermediate 38 (1.02 g) in DMF (2 ml) was added to a stirred solution of N-[5-(2-amino-1hydroxyethyl)-2hydroxyphenyl]methanesulphonamide (1.5 g) and DEA (1.55 g) in dry DMF (20 ml) at 100° and the resulting red solution was stirred at 100° for 2 h. The solvent was evaporated and the residue was purified by FCC eluting with System A (80:20:1) followed by trituration with dry ether to give the title compound as a fawn powder (390 mg) m.p. 85°-87°. T.l.c. (System A 80:20:1) Rf 0.19.

EXAMPLE 27

5-[2-[[6-[[2-(4-Amino-3,5-dichlorophenyl)-2-hydroxyethyl]amino]hexyl]oxy]ethyl]-$\underline{N},\underline{N}$-diethyl-2-thiophenecarboxamide, (E)-butenedioate salt (2:1)

A solution of Intermediate 16 (0.47 g), 5-[2-[(6-bromohexyl)oxy]ethyl]-2-$\underline{N},\underline{N}$-diethylthiophenecarboxamide (0.55 g) and DEA (0.22 g) in DMF (10 ml) was treated according to the method of Example 25 except the FCC eluant was System C (98:2:1→95:5:1). The title compound was obtained as a white solid (437 mg), m.p. 112°-113°.

Analysis: Found: C,54.9; H,6.7; N,7.0; Cl,11.9.
$C_{25}H_{37}Cl_2N_3O_3S.0.5C_4H_4O_4$ requires C,55.1; H,6.7; N,7.1; Cl,12.0%.

EXAMPLE 28

5-[2-[[6-[[2-(4-Amino-3,5-dichlorophenyl)-2-hydroxyethyl]amino]hexyl]oxy]ethyl]-2thiophenemthanol, (E)-butenedioate salt (2:1)

A solution of Intermediate 16 (0.98 g), 5-[2-[(6-bromohexyl)oxy]ethyl]-2-thiophenemthanol (0.95 g) and DEA (0.46 g) in DMF (18 ml) was treated according to the method of Example 25 except that the FCC eluant was System C (98:2:1→95:5:1). The title compound was obtained as a cream solid (0.635 g), m.p. 108°-109°.

Analysis: Found: C,52.3; H,6.1; N,5.1; Cl,13.61
$C_{21}H_{30}Cl_2N_2O_3S.0.5C_4H_4O_4 0.5H_2O$ requires C,52.3; H,6.3; N,5.3; Cl,13.4%

EXAMPLE 29

Methyl 5-[2-[[6-[[2-(4-Amino-3,5-dichlorohenyl)2-hydroxyethyl]amino]hexyl]oxy]ethyl]-2-thiohenecarboxylate A solution of Intermediate 16 (1.19 g), methyl 5-[2-[(6-bromohexyl)oxy]ethyl]-2thiophenecarboxylate (1.25 g) and DEA (0.56 g) in DMF (20 ml) was stirred at ca 100° for 2.5 h. The solvent was evaporated in vacuo and the residue purified by FCC eluting with System C (98:2:1→95:5:1) to give a yellow oil. Trituration with hexane-ether (5:1) gave the title compound as an off-white solid (0.839 g), m.p. 77.5°-78.5°.

Analysis: Found: C,53.85; H,6.09; N,5.62; Cl,14.75.
$C_{22}H_{30}Cl_2N_2O_4S$ requires C,53.99; H,6.18; N,5.72; Cl,14.49%.

EXAMPLE 30

5-[2-[[6-[[2-(4-Amino-3,5-dichlorohphenyl)-2-hydroxyethyl]amino]hexyl]oxy]ethyl]-2-thiophenecarbyxlic acid A solution of methyl 5-[2-[[6-[[2-(4-amino-3,5-dichlorophenyl)-2-hydroxyethyl]amino]hexyl]oxy]ethyl]-2-thiohenecarboxylate (0.274 g) in a 2N sodium solution (4.5 ml) and methanol (20 ml) was stirred at room temperature under nitrogen for 28 h. Dowex 50 (H+) methanol-washed ion exchange resin was added portionwise to neutralise the mixture to pH7. The mixture was filtered and evaporated in vacuo to give an orange solid. Trituration with hexane gave the title compound as a yellow solid (229 mg), m.p. 178°-185° (decomp.)

Analysis: Found: C,52.0; H,6.0; N,5.6; Cl,14.2
$C_{21}H_{28}Cl_2N_2O_4S.0.5H_2O$ requires C,52.1; H,6.0; N,5.8; Cl,14.6%.

EXAMPLE 31

$\underline{N},\underline{N}$-Diethyl-5-[2-[[2-(4-amino-3,5-dichlorophenyl)-2-hydroxyethyl]amino]pentyl]oxy]ethyl]-2-thiophenesulphonamide (E)-butenedioate salt (2:1)

A solution of Intermediate 16 (0.48 g), 5-[2-[(5-bromopentyl)(oxy]ethyl]-2$\underline{N},\underline{N}$-diethylthiophenesulphonamide (0.6 g) and DEA (0.23 g) in DMF (10 ml) was stirred at ca 100° for 3.5 h under nitrogen. The solvent was evaporated in vacuo to give a brown oil. Purification by FCC eluting with System C (95:5:1), gave a yellow oil which was dissolved in methanol (30 ml) and treated with fumaric acid (0.043 g), evaporated in vacuo and triturated with ether to give the title compound as a cream solid (0.531 g), m.p. 127°-129°.

Analysis: Found: C,49.0; H,6.3; N,6.5; Cl,11.6.
$C_{23}H_{35}Cl_2N_3O_4S_2.0.5C_4H_4O_4$ requires C,49.2; H,6.1; N,6.9; Cl,11.6%

EXAMPLE 32

$\alpha^1$-[[[6-[2-Benzo[b]thienyl]ethoxy]hexyl]amino]methyl]-4-hydroxy-1,3 -benzenedimethanol, 4,4'-metylenebis(3-hydroxy-2-naphthalenecarboxylate)- salt (2:1)

A solution of $\alpha^1$-[[[6-[2-(2-benzo[b]thienyl)ethoxy]-hexyl]amino]methyl]-4-hdyroxy-1,3-benzenedimethanol (0.378 g) in methanol (20 ml) was treated with 4,4'-methylenebis (3-hydroxy-2-napthalene carboxylic acid) (165 mg) and heated at reflux for 1 h. The mixture was cooled to room temperature, filtered and evaporated in vacuo. Trituration with dry ether afforded the title compound as a yellow foam (380 mg) m.p. 86°-93°.

Analysis: Found: C,67.9; H,6.8; N,2.15; S,4.9.
$C_{25}H_{38}NO_4S.0.5C_{23}H_{16}O_6.0.4H_2O$ requires C,68.0; H,6.5; N,2.2; S,5.0%.

The following are examples of suitable formulations of compounds of the invention. The term 'active ingredient' is used herein to represent a compound of the invention.

| Tablets (Direct Compression) | |
|---|---|
| | mg/tablet |
| Active ingredient | 2.0 |
| Microcrystalline cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcyrstalline cellulose or the compression weight and using punches to suit.

The tablets may be film coated with suitable film forming materials, such as hydroxypropylmethylcellulose, using standard techniques. Alternatively, the tablets may be sugar coated.

| Metered Dose Pressurised Aerosol (Suspension Aerosol) | | |
|---|---|---|
| | mg/metered dose | Per can |
| Active ingredient | 0.100 | 26.40 mg |

-continued

| Metered Dose Pressurised Aerosol (Suspension Aerosol) | | |
|---|---|---|
| | mg/metered dose | Per can |
| micronised Oleic Acid BP | 0.010 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°–15° C. and the micronised drug is mixed into the solution with a high shear mixer. The suspension is metered into aluminium aerosol cans and suitable metering valves delivering 85 mg of suspension are crimped onto the cans and the dichlorodifluoromethane is pressure filled into the cans through the valves.

| Inhalation Cartridges | |
|---|---|
| | mg/cartridge |
| Active ingredient micronised | 0.200 |
| Lactose BP to | 25.0 |

The active ingredient is micronised in fluid energy mill to a fine particle size range prior to blending with normal tabletting grade lactose in a high energy mixer. The powder blend is filled into No. 3 hard gelatin capsules on a suitable encapsulating machine. The contents in the cartirdges are administered using a powder inhaler such as the Glaxo Rotahaler.

We claim:

1. A compound of formula (I)

$$Ar-\overset{R^{18}}{\underset{OH}{C}}H\overset{}{C}HNH\overset{R^1}{\underset{R^2}{C}}XCH_2OCH_2YQ$$

or a physiologically acceptable salt or hydrate thereof, wherein

Ar represents (a)

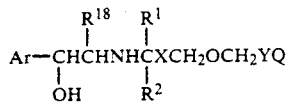

where $R^3$ is a straight or branched $C_{1-3}$alkylene group,

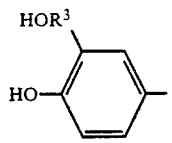

where one of $R^4$ and $R^5$ is a hydroxy group and the other is a hydrogen or halogen atom or a hydroxy group,

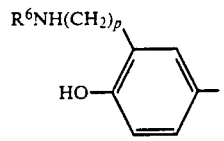

where $R^6$ is a group $R^7CO-$, $R^7NHCO-$, $R^7R^8NSO_2-$ or $R^9SO_2-$ (where $R^7$ and $R^8$ each represent a hydrogen atom or a $C_{1-3}$alkyl group and $R^9$ is a $C_{1-3}$alkyl group) and p is an integer 0 or 1,

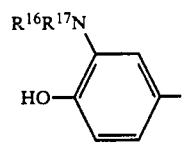

where $R^{16}$ and $R^{17}$ each represent a hydrogen atom or a $C_{1-4}$alkyl group, or, when $R^{16}$ is a hydrogen atom, $R^{17}$ may also represent a $C_{1-4}$alkoxycarbonyl group,

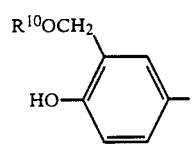

where $R^{10}$ is a $C_{1-3}$alkyl group,

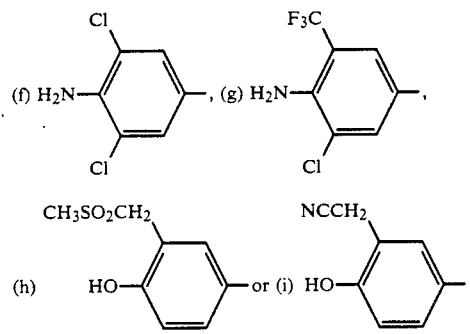

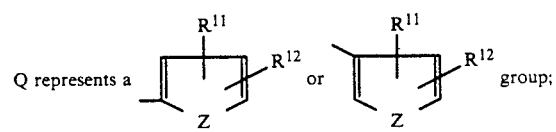

X represents a bond or a $C_{1-7}$alkylene, $C_{2-7}$alkenylene or $C_{2-7}$alkynylene chain, Y represents a bond or a $C_{1-6}$alkylene, $C_{2-6}$alkenylene or $C_{2-6}$alkynylene chain, with the proviso that the sum total of carbon atoms in X and Y is 2 to 100;

$R^1$ and $R^2$ each represents a hydrogen atom or a $C_{1-3}$alkyl group with the proviso that the sum total of carbon atoms in $R^1$ and $R^2$ is not more than 4;

$R^{18}$ represents hydrogen or $C_{1-3}$alkyl;

Q represents a $$\begin{array}{c} R^{11} \\ \diagup\!\!\!\diagdown R^{12} \\ Z \end{array} \text{ or } \begin{array}{c} R^{11} \\ \diagup\!\!\!\diagdown R^{12} \\ Z \end{array} \text{ group};$$

Z represents a sulphur atom;

$R^{11}$ represents hydrogen or halogen atom or a group $C_{1-3}$alkyl, nitro-$(CH_2)_rR$, $-(CH_2)_rCOR^{13}$, or $SO_2NR^{14}R^{15}$;

$R^{12}$ represents a hydrogen atom or a $C_{1-3}$alkyl group, or, when $R^{11}$ represents a halogen atom, $R^{12}$ additionally represents a halogen atom;

R represents a hydroxy, $C_{1-3}$alkoxy or $NR^{14}R^{15}$ group;

$R^{13}$ represents hydroxy, $C_{1-4}$alkoxy or $NR^{14}R^{15}$ group;

$R^{14}$ and $R^{15}$ each represents a hydrogen atom or a $C_{1-4}$alkyl group;

t represents an integer from 1 to 3;

r represents an integer from 0 to 3.

2. A compound according to claim 1 wherein Ar is selected from

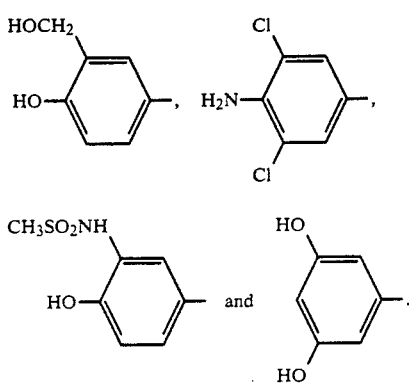

3. A compound according to claim 1 wherein X and Y are both alkylene.

4. A compound according to claim 1 wherein $R^1$ and $R^2$ are both hydrogen.

5. A compound according to claim 1 wherein $R^{18}$ is hydrogen.

6. A compound according to claim 1 wherein Q is

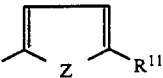

7. A compound selected from:

4-hydroxy-$\alpha^1$-[[[6-[3-(3-thienyl)propoxy]hexyl]amino]methyl]-1,3-benzenedimethanol;

5-[1-hydroxy-2-[[6-[[4-(2-thienyl)butoxy]hexyl]amino]ethyl]-1,3-benzenediol;

4-hydroxy-$\alpha^1$-[[[6-[4-(2-thienyl)butoxy]hexyl]amino]methyl]-1,3-benzenedimethanol;

$\alpha^1$-[[[1,1-dimethyl-6-[2-(2-thienyl)ethoxy]hexyl]amino]methyl]-4-hydroxy-1,3-benzenedimethanol;

5-[2-[[6-[[2-(4-amino-3,5-dichlorophenyl)-2-hydroxyethyl]amino]hexyl]oxy]ethyl]-N,N-diethyl-2-thiophenecarboxamide;

and their physiologically acceptable salts and hydrates.

8. A method for the treatment of a mammal suffering from a condition susceptible to amelioration by stimulation of a $\beta_2$-adrenoreceptor comprising administering an effective amount of a compound of formula (I) as defined in claims 1 or 7.

9. A pharmaceutical formulation comprising a $\beta_2$-adrenoreceptor stimulating amount of a compound of formula (I) as defined in claims 1 or 7 together with a physiologically acceptable carrier or excipient.

10. A method according to claim 8, wherein the mammal is man.

* * * * *